United States Patent [19]

Kaplan et al.

[11] 4,254,102
[45] Mar. 3, 1981

[54] SUBSTANTIVE PABA COMPOSITIONS

[75] Inventors: Carl Kaplan; Edward Marlowe, both of Memphis; Robert M. Sayre, Germantown, all of Tenn.

[73] Assignee: Plough, Inc., Memphis, Tenn.

[21] Appl. No.: 611,293

[22] Filed: Sep. 8, 1975

[51] Int. Cl.³ .......................... A61K 7/42; A61K 7/44
[52] U.S. Cl. ........................................ 424/59; 424/60; 424/317; 424/318; 424/361
[58] Field of Search .................... 424/60, 59, 317, 318

[56] References Cited

U.S. PATENT DOCUMENTS

| | | | |
|---|---|---|---|
| 1,888,601 | 11/1932 | Mack et al. | 424/310 X |
| 2,340,776 | 2/1944 | Stamborsky | 424/310 X |
| 2,382,546 | 8/1945 | Curtis | 424/310 X |
| 2,457,188 | 12/1948 | Stone | 424/310 |
| 3,011,950 | 12/1961 | Mehaffey | 424/59 X |
| 3,068,153 | 12/1962 | Morehouse | 424/59 |
| 3,080,295 | 3/1963 | Goorley | 424/59 X |
| 3,479,428 | 11/1969 | Bryce et al. | 424/310 |
| 3,821,363 | 6/1974 | Black et al. | 424/60 X |

FOREIGN PATENT DOCUMENTS

| | | | |
|---|---|---|---|
| 1717102 | 3/1972 | Fed. Rep. of Germany | 424/60 |
| 1162337 | 8/1969 | United Kingdom | 424/60 |

OTHER PUBLICATIONS

Manufacturing Chemist, 12/1953, p. 534.
Modern Cosmeticology, vol. I, 1955, p. 265, Harry.

*Primary Examiner*—Dale R. Ore
*Attorney, Agent, or Firm*—Bruce M. Eisen; Vincent H. Gifford

[57] ABSTRACT

Novel topical sun-protective PABA formulations are provided which retain good protective index levels, even after moisture exposure. These cosmetically elegant formulations contain certain fatty alcohols and nonionic surfactants, and preferably certain cellulosics.

12 Claims, No Drawings

SUBSTANTIVE PABA COMPOSITIONS

This invention relates to improved PABA compositions which afford significantly greater substantivity to wet skin. In addition, these compositions are also more cosmetically elegant.

Para-aminobenzoic acid is widely recognized as an excellent sun-blocking agent and generally referred to in this context simply as PABA. There are many individuals who are fair-skinned or otherwise especially susceptible to the deleterious effects of prolonged exposure to sunlight who should and do use PABA formulations. Existing PABA formulations are generally available in the form of 70% alcoholic solutions. One problem with such solutions is that their initial high substantivity to the skin is substantially diminished by perspiration or swimming. Typically, the protective index (PI) of an applied PABA formulation may drop from about 10 to 3 after swimming. The high substantivity of PABA to the skin from a simple 70 to 95% ethanol solution is taught in the art to be markedly reduced by the addition of common additives such as emollients, e.g. cetyl alcohol. See the standard reference work *Cosmetic Science and Technology*, Volume 1, Second Edition, 1972 (edited by Balsam and Sagarin) p. 294.

A further disadvantage of current alcoholic PABA lotions is their fluidity, i.e. low viscosity. Thus application of the product is difficult to control and its lack of "body, texture or feel" renders it cosmetically inelegant.

We have surprisingly found that one can prepare cosmetically elegant PABA formulations whose substantivity to wet skin is significantly enhanced by incorporating therein both 2 to 6% by weight of a cosmetically acceptable solid fatty alcohol having 12 to 18 carbon atoms and 0.5 to 2% of a cosmetically acceptable nonionic surfactant of the polyethenoxy type having an HLB value within the range of about 9 to 18. The weight ratio of said alcohol to surfactant should be in the range of 2–6 to 1 and preferably about 4 to 1.

Such cosmetically acceptable fatty alcohols which are solid (i.e., at 20° C.) are well known in the art, such as 1-hexadecanol and 1-octadecanol. The preferred alcohol is cetyl alcohol, N.F. also known as cetostearyl alcohol, or in CTFA terminology, cetearyl alcohol.

A preferred subclass of nonionic surfactants are the polyoxyethylene ethers of cosmetically acceptable alcohols having 12 to 18 carbon atoms. Exemplary of these are ethoxylated coconut alcohol, e.g. coceth-6, ceteareth-5, ceteth-20, and steareth-20. Other utilizable subclasses are the esters of a polyethylene glycol having a molecular weight between about 200 and 600 with a fatty acid having 12 to 18 carbon atoms, e.g. polyethylene glycol 400 monolaurate; and polyethenoxy ethers of esters of sorbitol with fatty acids having 12 to 18 carbon atoms, e.g. polysorbate-80. The most preferred nonionic surfactant for use in the compositions of this invention is coceth-6. All ingredients are specified in accordance with the recommended terminology of the CTFA Cosmetic Ingredient Dictionary.

The aqueous compositions of our invention should contain about 45 to 65% by weight of ethanol. The amount of PABA should be in the range of 2 to 10% by weight and preferably around 5%. Water comprises the balance of the vehicle and represents about 25 to 50% of the total composition weight and preferably 30 to 40%. The formulations of this invention are more viscous than the standard alcoholic solutions, thus permitting easier and more elegant application to the skin.

This beneficent inclusion of the above surfactants is surprising in view of the art, e.g. U.S. Pat. No. 3,697,644. This patent, directed to preparing cosmetic compositions of increased substantivity, teaches both the inclusion of protective colloids (e.g. cellulosics) and the avoidance of surfactants and states "Because of the absence of any surface active agent the film cannot easily be removed with water." Contrary to our use of ethanol, the patentees therein employ a solvent which has little or no water solubility.

Another problem with the current PABA lotions is the real possibility of the user leaving bare spots (i.e. unprotected skin areas that are not easily visible as such). If desired, one can add compatible pigments or nonionic surfactants to the composition of our invention to permit the production of an opaque lotion, thereby enabling the user to clearly see that all appropriate skin areas have been treated. Titanium dioxide is exemplary of such pigments. The addition of compatible opacifying additives to our compositions does not, as might be expected, significantly diminish substantivity.

In a preferred embodiment, the compositions of this invention also contain 0.1 to 2% by weight of a cosmetically acceptable, water-soluble cellulosic polymer. This results in a still further enhancement of substantivity, as well as increased viscosity. Exemplary of these are hydroxypropyl cellulose, methylcellulose and hydroxyethylcellulose, with the latter being preferred. These cellulosics should be present in the amount of 0.1 to 2% by weight of the total composition. The optimum molecular weight range of the chosen cellulosic depends on the totality of the formulation and the desired cosmetic profile and can be readily determined by the skilled formulator.

Other ingredients commonly used in sun-protective compositions can be used for their well known purposes in their art-recognized amounts, for example emollients and humectants such as polyoxyethylene 400 (PEG-8) and diisopropyl adipate; preservatives (e.g. methyl and propyl paraben); and perfumes.

In another aspect this invention provides a water-resistant method for protecting human skin against actinic radiation comprising evenly applying to said skin a composition of this invention.

EXAMPLE

A substantive sun-block lotion having the following percentage composition is prepared. All parts throughout this specification are by weight unless otherwise indicated.

| | |
|---|---|
| PABA | 5.0% |
| cetyl alcohol, N.F. | 3.6% |
| coceth-6 | 0.9% |
| hydroxyethylcellulose | 0.6% |
| PEG-8 | 1.0% |
| perfume | 0.4% |
| titanium dioxide | 0.15% |
| ethanol | 53.5% |
| water (balance) | ~35% |

The particular hydroxyethylcellulose in the above example has a viscosity of 4,000 to 5,200 cps at 25° C. in a 1% solution when measured by means of a standard LVF Brookfield measurement and is commercially available under the trade name "Cellosize QP-100M" from Union Carbide Corporation.

This exemplary formulation can be prepared as follows. Add 0.6 g. hydroxyethylcellulose to 32.7 g. water and heat at 80° C. with stirring for 15 minutes. Heat to 80° C. a 4:1 mixture of the cetyl alcohol and coceth-6 and add this, while agitating, to the foregoing hydroxyethylcellulose mixture. Cool the resultant emulsion to 28° C.

To a separate kettle add 53.5 g. ethanol, 0.4 g. perfume and 7.2 g. of PABA in the form of a wet paste (containing 78.6% PABA). Continue agitation until the paste dissolves while maintaining the temperature at about 28° C. and then filter. Add this filtered mixture to the above emulsion while agitating and maintaining the temperature at about 28° C.

Into a separate pot add 1 g. of PEG-8 and 0.15 g. titanium dioxide and homogenize until a uniform suspension results. Add this suspension to the foregoing mixture and homogenize, while agitating, until well blended.

The resultant lotion is opaque and cosmetically elegant. It has a protective index of about 10. After a standard wash off test, the protective index is reduced to about 5–7. Similar results are obtained by substituting an equivalent amount of ceteareth-5 for coceth-6.

In another embodiment of this invention we have found that sunscreen agents of the benzophenone class can be compatibly incorporated in the formulations of this invention to substantially increase the protective index as well as broaden the ultraviolet spectrum against which these formulations protect. This is of particular value to certain users who are sensitive to actinic radiation of higher wave length then PABA protects against. Exemplary of these benzophenone sunscreens are the series benzophenone-1 through benzophenone-12. Benzophenone-8 (i.e., 2,2-dihydroxy-4-methoxybenzophenone) is the preferred benzophenone for use in the formulations of this invention. The amount of this benzophenone sunscreen ingredient should be in the range of 0.5 to 5% by weight.

Numerous variants of the above formulations and methods of their use will be apparent to those skilled in the art within the spirit of this invention.

We claim:

1. A cosmetically elegant, substantive, sun-protective aqueous composition comprising by weight 2 to 10% PABA and 2 to 6% of a cosmetically acceptable $C_{12}$–$C_{18}$ fatty alcohol which is solid at 20° C. and 0.5 to 2% of a cosmetically acceptable nonionic surfactant of the polyoxyethylene type having an HLB value of between about 9 and 18, the ratio of said alcohol to surfactant being in the range of 2–6 to 1, and about 45 to 65% ethanol with the balance of the vehicle being substantially water.

2. A composition according to claim 1 wherein said surfactant is a polyoxyethylene ether of a cosmetically acceptable alcohol having 12 to 18 carbon atoms.

3. A composition according to claim 1 wherein said fatty alcohol is cetearyl alcohol.

4. A composition according to claim 1 wherein said fatty alcohol to surfactant ratio is about 4 to 1.

5. A composition according to claim 1 which additionally contains 0.5 to 5% of a water-soluble cellulosic polymer.

6. A composition according to claim 5 wherein said cellulosic polymer is hydroxyethylcellulose.

7. A composition according to claim 3 wherein said surfactant is coceth-6.

8. A composition according to claim 3 wherein said surfactant is ceteareth-5.

9. A composition according to claim 1 which additionally contains titanium dioxide.

10. A composition according to claim 1 which additionally contains 0.5 to 5% of a dermatogically acceptable sunscreen of the benzophenone group.

11. A composition according to claim 10 wherein said benzophenone is benzophenone-8.

12. A water-resistant method for protecting the skin against actinic radiation comprising evenly applying to said skin a composition of claim 1.

* * * * *